United States Patent
Brown et al.

(10) Patent No.: US 12,102,814 B2
(45) Date of Patent: Oct. 1, 2024

(54) ALGORITHM FOR DETECTING AND PRESENTING SUCTION IN DOWN-SAMPLED MCS LOG FILES

(71) Applicant: HeartWare, Inc., Miami Lakes, FL (US)

(72) Inventors: Michael C. Brown, Dresher, PA (US); Veronica Ramos, Homestead, FL (US); Neil Voskoboynikov, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 516 days.

(21) Appl. No.: 17/193,548

(22) Filed: Mar. 5, 2021

(65) Prior Publication Data

US 2021/0321881 A1    Oct. 21, 2021

Related U.S. Application Data

(60) Provisional application No. 63/010,848, filed on Apr. 16, 2020.

(51) Int. Cl.
*A61M 60/122*    (2021.01)
*A61B 5/0215*    (2006.01)
(Continued)

(52) U.S. Cl.
CPC ........ *A61M 60/538* (2021.01); *A61M 5/1428* (2013.01); *A61M 60/126* (2021.01);
(Continued)

(58) Field of Classification Search
CPC .............. A61M 60/126; A61M 60/592; A61M 60/585; A61M 60/538; A61M 5/1428; A61M 2205/3334
See application file for complete search history.

(56) References Cited

U.S. PATENT DOCUMENTS 9,492,601 B2    11/2016    Casas et al.
9,623,161 B2    4/2017    Medvedev et al.
(Continued)

OTHER PUBLICATIONS

International Search Report and Written Opinion dated Jun. 8, 2021, for corresponding International Application No. PCT/US2021/024821; International Filing Date: Mar. 30, 2021 consisting of 9-pages.

*Primary Examiner* — Pamela M. Bays
(74) *Attorney, Agent, or Firm* — Shumaker & Sieffert, P.A.

(57) ABSTRACT

A method of determining a presence of suction in a patient having an implantable blood pump from down-sampled log files. The method comprising calculating a waveform index for each of a plurality of flow rate data points from the down-sampled log files. The calculated waveform index is compared with a predetermined waveform index threshold. A non-suction trough baseline is calculated from the plurality of flow rate data points. A difference between a measured trough and a calculated non-suction trough baseline is compared with a predetermined threshold. The presence of suction for each of the plurality of flow rate data points is determined if the calculated waveform index is greater than the predetermined waveform index threshold and the difference between the measured trough and a calculated non-suction trough baseline is greater than the predetermined threshold.

16 Claims, 5 Drawing Sheets

(51) Int. Cl.
  *A61M 5/142*    (2006.01)
  *A61M 60/126*   (2021.01)
  *A61M 60/538*   (2021.01)
  *A61M 60/585*   (2021.01)
  *A61M 60/592*   (2021.01)
  *A61B 5/00*     (2006.01)

(52) U.S. Cl.
  CPC ........ *A61M 60/585* (2021.01); *A61M 60/592*
        (2021.01); *A61B 5/0031* (2013.01); *A61B*
        *5/0215* (2013.01); *A61B 5/686* (2013.01);
                  *A61M 2205/3334* (2013.01)

(56) References Cited

U.S. PATENT DOCUMENTS

| | | |
|---|---|---|
| 9,795,726 B2 | 10/2017 | Brown et al. |
| 10,434,234 B2 | 10/2019 | Brown et al. |
| 2004/0215050 A1* | 10/2004 | Morello .............. A61M 60/538 600/17 |
| 2015/0367048 A1* | 12/2015 | Brown ................ A61M 60/148 600/16 |
| 2016/0058930 A1 | 3/2016 | Medvedev et al. |
| 2018/0015213 A1 | 1/2018 | Brown et al. |
| 2018/0028738 A1 | 2/2018 | Brown et al. |
| 2019/0237175 A1 | 8/2019 | Brown et al. |
| 2019/0351116 A1 | 11/2019 | Kudlik |

* cited by examiner

ALGORITHM FOR DETECTING AND PRESENTING SUCTION IN DOWN-SAMPLED MCS LOG FILES

CROSS-REFERENCE TO RELATED APPLICATION

This application claims the benefit of U.S. application Ser. No. 63/010,848 filed Apr. 16, 2020.

FIELD

The present technology is generally related to implantable blood pumps, and in particular, detecting suction in down-sampled log files.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta. To provide clinically useful assistance to the heart, blood pumps impel blood at a substantial blood flow rate. For an adult human patient, a ventricular assist device may be arranged to pump blood at about 1-10 liters per minute at a differential pressure across the pump of about 10-110 mm Hg, depending on the needs of the patient. The needs of the patient may vary with age, height, and other factors.

If a VAD is operated at a flow rate in excess of the inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline. If the flow rate through the pump is insufficient, the device will not provide sufficient circulatory assistance to the patient.

SUMMARY

The techniques of this disclosure generally relate to implantable blood pumps, and in particular, detecting suction in down-sampled log files.

In one aspect, the present disclosure provides a method of determining a presence of suction in a patient having an implantable blood pump from down-sampled log files. The method comprising calculating a waveform index for each of a plurality of flow rate data points from the down-sampled log files. The calculated waveform index is compared with a predetermined waveform index threshold. A non-suction trough baseline is calculated from the plurality of flow rate data points. A difference between a measured trough and a calculated non-suction trough baseline is compared with a predetermined threshold. The presence of suction for each of the plurality of flow rate data points is determined if the calculated waveform index is greater than the predetermined waveform index threshold and the difference between the measured trough and a calculated non-suction trough baseline is greater than the predetermined threshold.

In another aspect of this embodiment, if suction is determined, the method further includes displaying each of the plurality of flow rate data points in a histogram on the down-sampled log-files.

In another aspect of this embodiment, displaying each of the plurality of flow rate data points in a histogram includes displaying a number of flow rate data points determined to be in suction during a predetermined number of data points divided by the predetermined number of data points.

In another aspect of this embodiment, the predetermined number of data points is 20.

In another aspect of this embodiment, calculating the non-suction trough baseline from the plurality of flow rate data points includes creating an array of non-suction trough baseline data points, the array only including data points in the plurality of flow rate data points whose calculated waveform index is below the predetermined waveform index threshold.

In another aspect of this embodiment, calculating the non-suction trough baseline from the plurality of flow rate data points includes calculating an average non-suction trough baseline from the array of non-suction trough baseline data points and subtracting from the calculated average non-suction trough baseline a standard deviation of the calculated average non-suction trough baseline multiplied by a standard deviation factor.

In another aspect of this embodiment, the standard deviation factor is 1.0.

In another aspect of this embodiment, the trough difference threshold is equal to 1.0.

In another aspect of this embodiment, the waveform index threshold is between 0.3 and 0.6.

In another aspect of this embodiment, the plurality of flow rate data points includes data sampled over the course of 24 hours.

In another aspect of this embodiment, the plurality of flow rate data points is equal to 96 data points.

In one aspect, a controller for an implantable blood pump includes processing circuitry being configured to calculate a waveform index for each of a plurality of flow rate data points from the down-sampled log files. The calculated waveform index is compared with a predetermined waveform index threshold. A non-suction trough baseline is calculated from the plurality of flow rate data points. A difference between a measured trough and a calculated non-suction trough baseline is compared with a predetermined threshold. The presence of suction for each of the plurality of flow rate data points is determined if the calculated waveform index is greater than the predetermined waveform index threshold and the difference between the measured trough and a calculated non-suction trough baseline is greater than the predetermined threshold.

In another aspect of this embodiment, if suction is determined, the controller is further configured to display each of the plurality of flow rate data points in a histogram on the down-sampled log-files.

In another aspect of this embodiment, displaying each of the plurality of flow rate data points in a histogram includes displaying a number of flow rate data points determined to be in suction during a predetermined number of data points divided by the predetermined number of data points.

In another aspect of this embodiment, the predetermined number of data points is 20.

In another aspect of this embodiment, calculating the non-suction trough baseline from the plurality of flow rate data points includes creating an array of non-suction trough baseline data points, the array only including data points in the plurality of flow rate data points whose calculated waveform index is below the predetermined waveform index threshold.

In another aspect of this embodiment, calculating the non-suction trough baseline from the plurality of flow rate data points includes: calculating an average non-suction trough baseline from the array of non-suction trough baseline data points and subtracting from the calculated average non-suction trough baseline a standard deviation of the calculated average non-suction trough baseline multiplied by a standard deviation factor.

In another aspect of this embodiment, the standard deviation factor is 1.0.

In another aspect of this embodiment, the trough difference threshold is equal to 1.0.

In one aspect, a controller for an implantable blood pump includes processing circuitry being configured to calculate a waveform index for each of a plurality of flow rate data points from the down-sampled log files. The calculated waveform index is compared with a predetermined waveform index threshold. A non-suction trough baseline is calculated from the plurality of flow rate data points, the calculation of the non-suction trough baseline including. An array of non-suction trough baseline data points is created, the array only including data points in the plurality of flow rate data points whose calculated waveform index is below the predetermined waveform index threshold. An average non-suction trough baseline is calculated from the array of non-suction trough baseline data points. A standard deviation of the calculated average non-suction trough baseline multiplied by a standard deviation factor is subtracted from the calculated average non-suction trough baseline. A difference between a measured trough and a calculated non-suction trough baseline is compared with a predetermined threshold. The presence of suction for each of the plurality of flow rate data points is determined if the calculated waveform index is greater than the predetermined waveform index threshold and the difference between the measured trough and a calculated non-suction trough baseline is greater than the predetermined threshold. If suction is determined, the controller is further configured to display each of the plurality of flow rate data points in a histogram on the down-sampled log-files.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
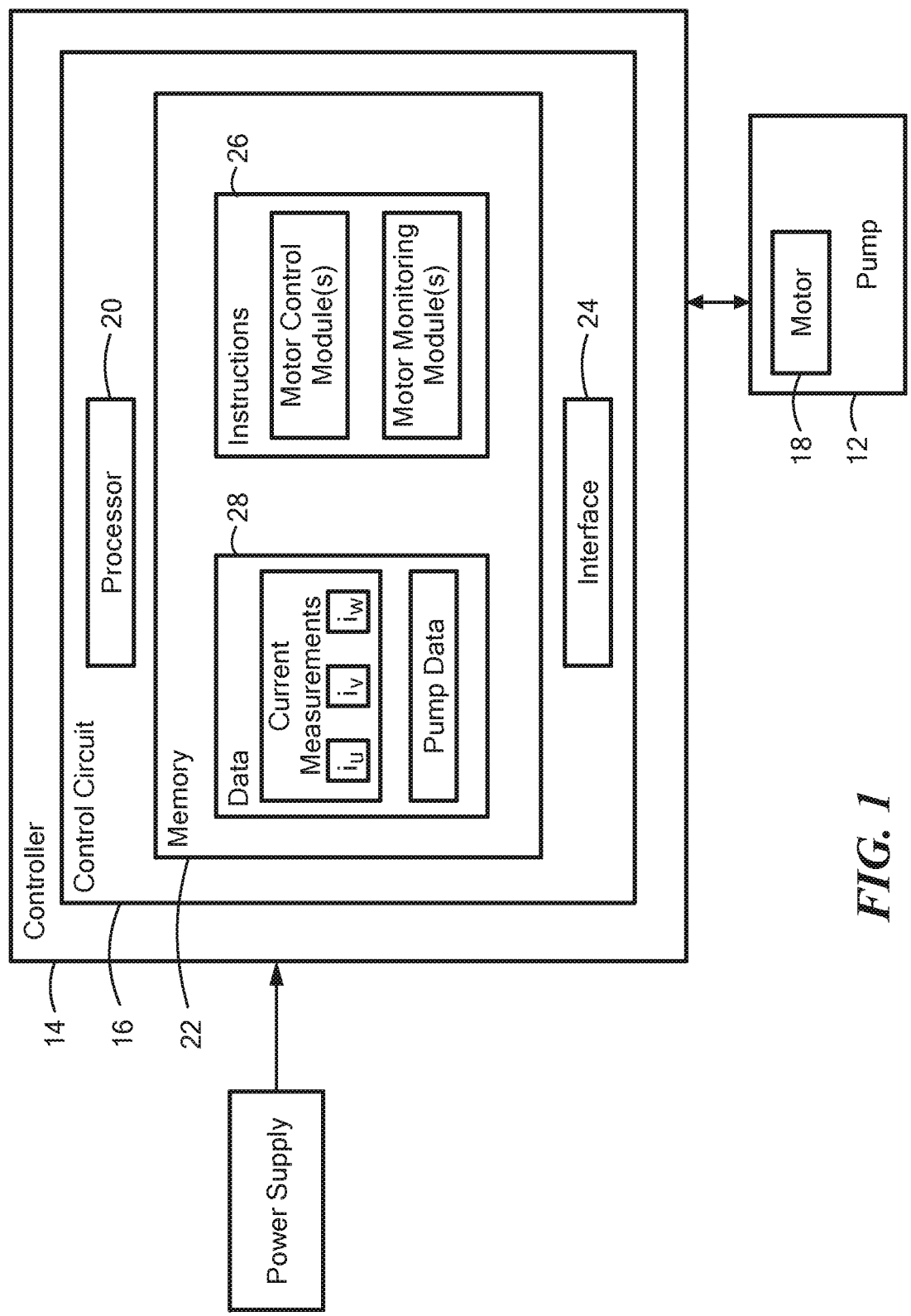
FIG. 1 is a block diagram of an exemplary system for an exemplary implantable blood pump.

FIG. 1 is a block diagram of the system 10 including an implantable blood pump 12 in communication with a controller 14. The blood pump 12 may be the HVAD® Pump or another mechanical circulatory support device fully or partially implanted within the patient and having a movable element, such as a rotor, configured to pump blood from the heart to the rest of the body. The controller 14 includes a control circuit 16 for monitoring and controlling startup and subsequent operation of a motor 18 implanted within the blood pump 12. The controller 14 may also include a processor 20, a memory 22, and an interface 24. The memory 22 is configured to store information accessible by the processor 20 including instructions 26 executable by the processor 20 and/or data 28 that may be retrieved, manipulated, and/or stored by the processor 20. In particular, the processor 20 includes circuitry configured to carry out the steps discussed herein with respect to the methods. As such, reference to the system 10 executing steps of the methods is intended to include the processor 20. Optionally, the method steps discussed below could be carried out by a remote computer having processing circuitry configured to analyze down-sampled log files, as discussed in more detail below.

Figure 2:
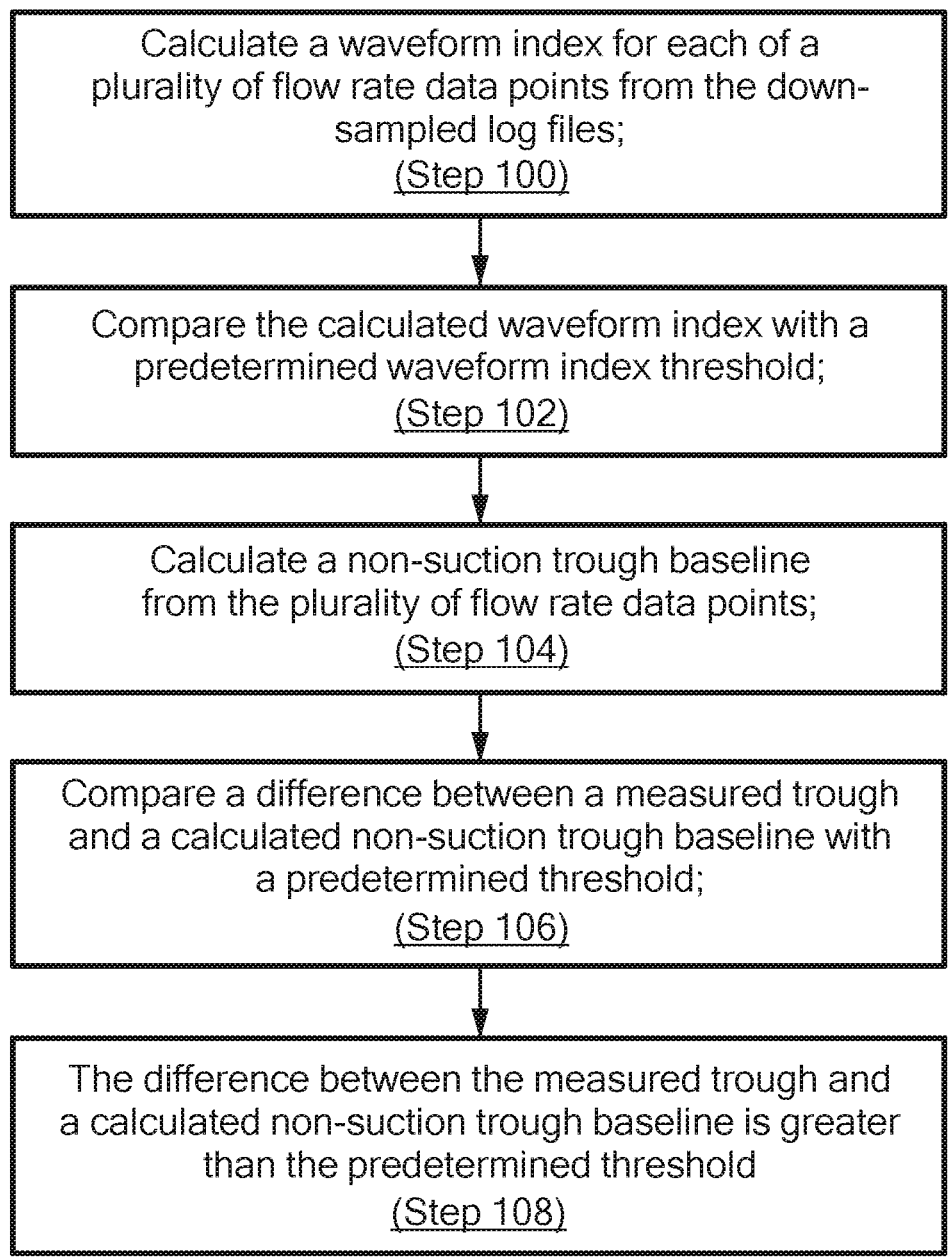
FIG. 2 is a flow chart showing an exemplary method of determined suction from down-sampled log files.
Figure 3:
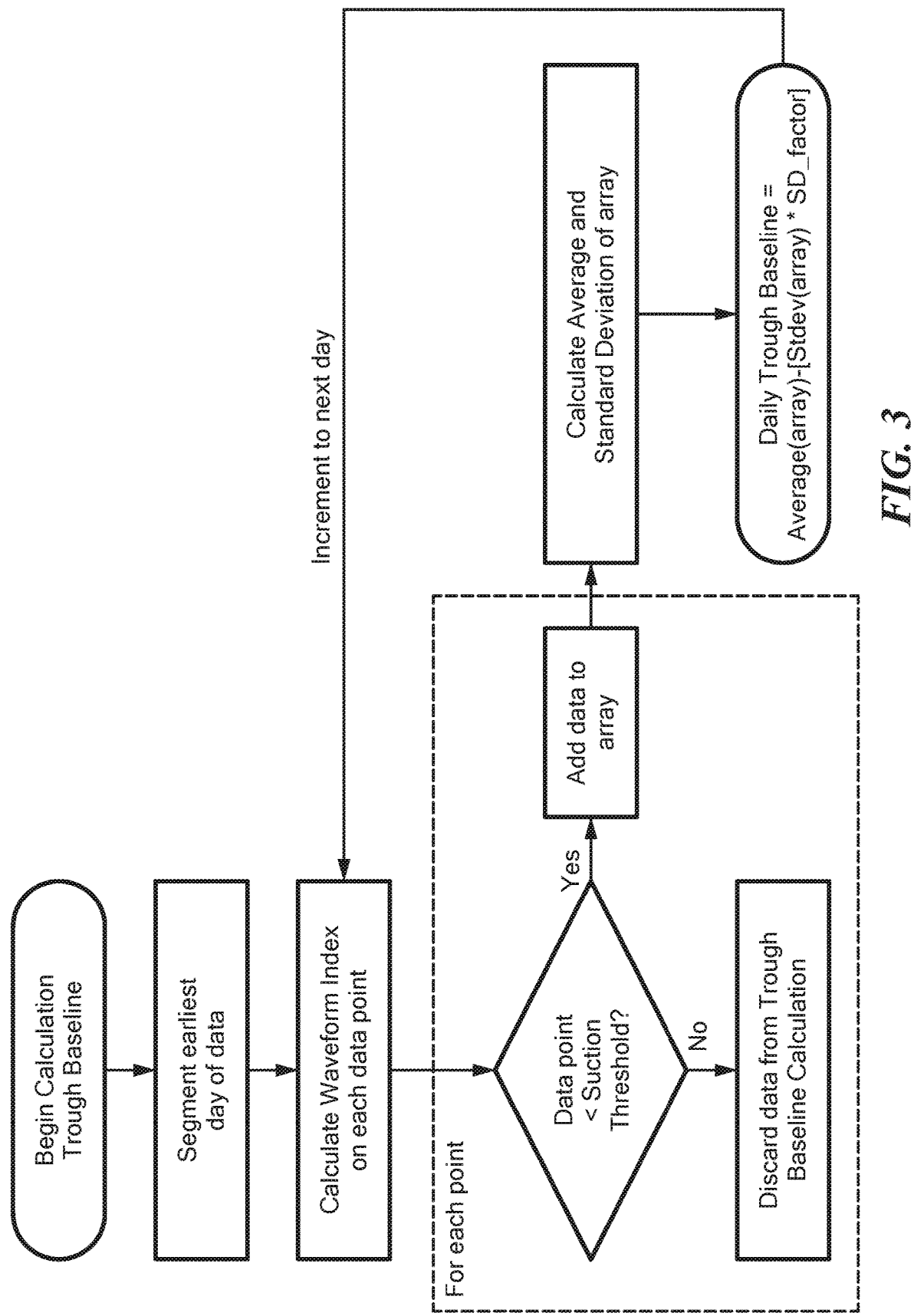
FIG. 3 is a flow chart showing an exemplary method of calculating a non-suction trough baseline.
Figure 4:
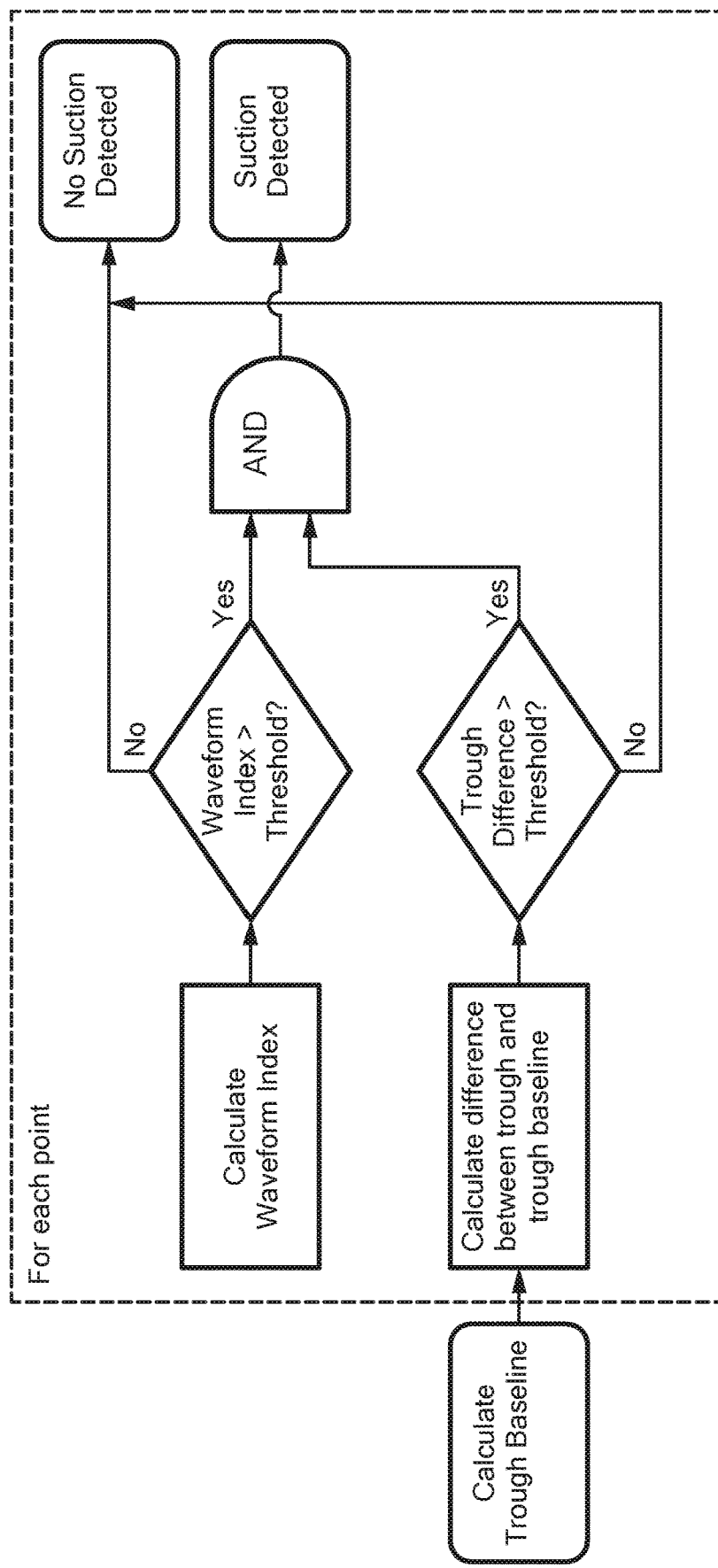
FIG. 4 a flow chart showing an exemplary method of determining suction using the non-suction trough baseline and calculated waveform index.

Referring now to FIGS. 2-4, the method includes calculating a waveform index for each of a plurality of flow rate data points from the down-sampled log files (Step 102). The waveform index is previously disclosed and described in U.S. Pat. No. 9,795,726, the entirety of which is expressly incorporated by reference herein. In particular, the waveform index is the average flow rate minus the trough flow rate divided by the pulsatility. The waveform index may be performed on each of a plurality of data points in a log-file for a given time window. For example, in one configuration, the controller samples pump 12 flow rate data for a two-second window every 15 minutes for a 24-hour period. Thus, in one configuration, 96 data points are used to calculate a waveform index for each data point although the time window and number of data points may vary, for example, a 12 hour period or 36 hour period and a two second window every 5 minutes. The calculated waveform index for each of the plurality of data points is then compared against a waveform index threshold (Step 102). For example, in one configuration, the waveform index threshold is predetermined and set at 0.48, although it could be any number. If the calculated waveform index is less than the threshold then no suction is indicated. If the calculated waveform index is greater than the waveform index threshold, then that data point is placed in an array to calculate a non-suction trough baseline, as discussed in more detail below.

Referring now to FIGS. 2-3, a non-suction trough baseline is calculated from the plurality of flow rate data points (Step 104). The non-suction trough baseline, like the waveform index, is based on the plurality of flow rate data points over a predetermined time window. For example, the non-suction trough baseline may be calculated daily based on the 96 data points discussed above. Only flow rate data points of the plurality of flow rate data points that are below waveform index threshold are included in the array. Of those data points that are not indicated to be suction, the non-suction trough baseline flow rate is calculated as an average of the included data points minus the standard deviation multiplied by a standard deviation factor. In an exemplary configuration, the standard deviation factor is 1.0, but may be any number.

Referring now to FIGS. 2 and 4, in an exemplary method of detecting suction from down-sampled log files, a difference between the trough data point and the calculated non-suction trough baseline is compared against a trough difference threshold (Step 106). In particular, if the difference between a trough data point and the non-suction trough baseline is greater than the trough difference threshold, then that data point is eligible to be flagged as a suction data point if for that same data point the calculated waveform index is greater the waveform index threshold. In another words, both the waveform index must be greater than the waveform index threshold and the difference between the trough data point and the trough baseline must be greater than the trough difference threshold for that data point to be flagged and labeled as suction (Step 108).

Figure 5:
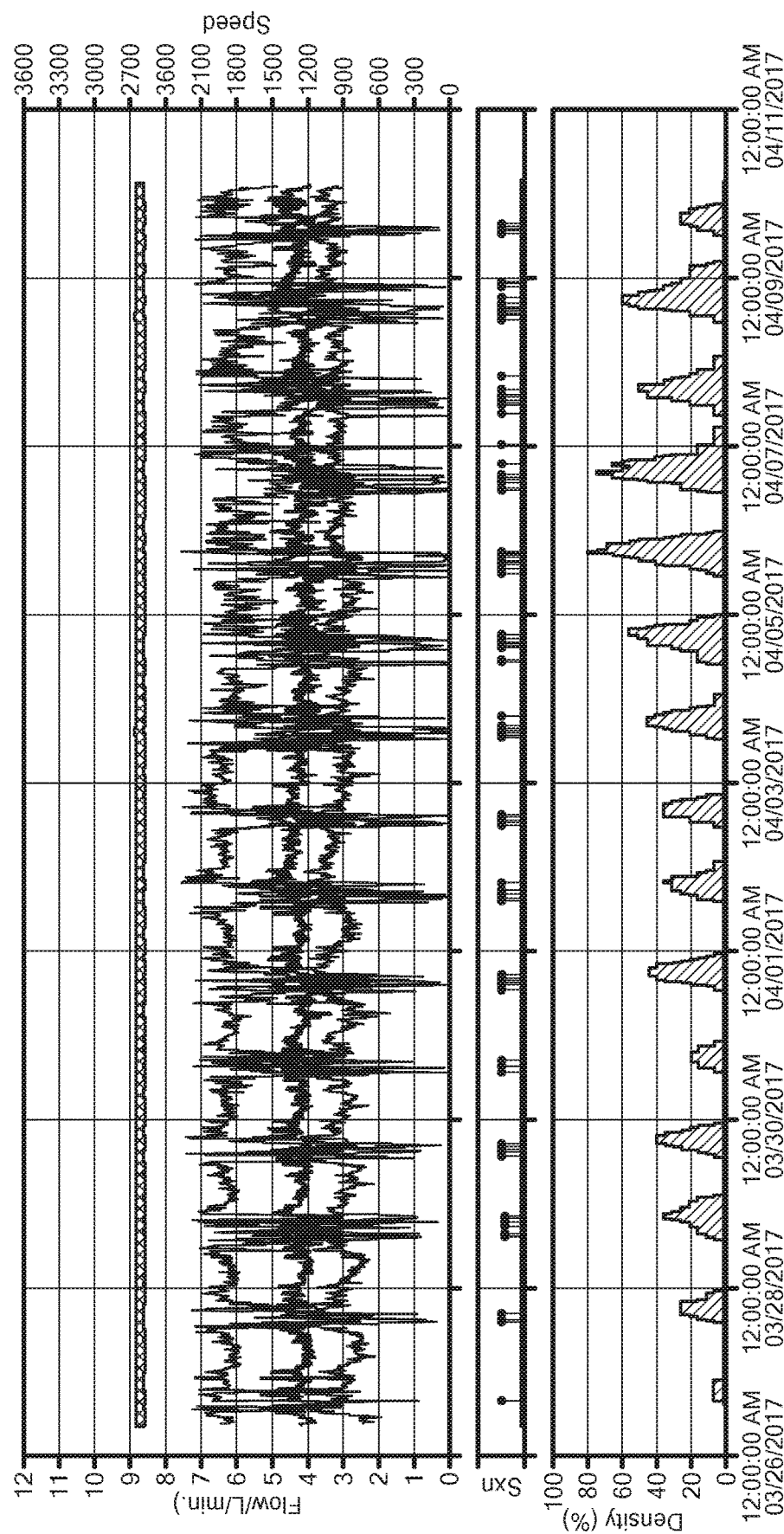
FIG. 5 is a graph showing a log file having a suction density displaying in the form of a histogram.

Referring now to FIG. 5, once a data point has been flagged as suction, it may be displayed in the form of a histogram as a measure of suction density. For example, as shown in FIG. 5 each of the plurality of flow rate data points indicated to be suction are displayed in a histogram on the down-sampled log-files. The presentation of the data includes displaying a number of flow rate data points determined to be in suction during a predetermined number of data points divided by the predetermined number of data points. For example, the algorithm may use 20, or less than 20, as the predetermined number of data point and the total number of those data points indicated to be in suction is the fact that is displayed in the form of density on the log-file beneath flow rate or current data. This enables the clinician to readily see when suction was most concentrated during a particular period of time.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable blood pump system, the system comprising:
    an implantable blood pump comprising a motor, the implantable blood pump being configured to cause blood flow in a patient; and
    a controller in communication with the implantable blood pump, the controller comprising processing circuitry configured to:
        calculate a waveform index for each of a plurality of flow rate data points from down-sampled log files, wherein each flow rate data point of the plurality of flow rate data points corresponds to a flow rate of the blood flow through the implantable blood pump;
        compare the calculated waveform index with a predetermined waveform index threshold;
        calculate a non-suction trough baseline from the plurality of flow rate data points;
        compare a difference between a measured trough and the calculated non-suction trough baseline with a predetermined threshold;
        determine for each of the plurality of flow rate data points whether a suction condition is present at the implantable blood pump, wherein the processing circuitry is configured to determine that the suction condition is present at the implantable blood pump for a flow rate data point in response to:
            the calculated waveform index being greater than the predetermined waveform index threshold; and
            the difference between the measured trough and the calculated non-suction trough baseline being greater than the predetermined threshold;
        determine a measure of suction density based on a number of the plurality of flow rate data points for which the suction condition is present and a total number of the plurality of flow rate data points; and
        cause a display device to output an indication of the measure of suction density experienced by the implantable blood pump.

2. The system of claim 1, wherein if the suction condition is determined for a flow data point of the plurality of flow rate data points, the processing circuitry is further configured to cause the display device to display the flow rate data point in a histogram on the down-sampled log files.

3. The system of claim 2, wherein displaying the flow rate data point in the histogram includes displaying a number of flow rate data points for which the suction condition is determined to be present during a predetermined number of data points divided by the predetermined number of data points.

4. The system of claim 3, wherein the predetermined number of data points is less than or equal to 20.

5. The system of claim 1, wherein calculating the non-suction trough baseline from the plurality of flow rate data points includes:

creating an array of non-suction trough baseline data points, the array only including data points in the plurality of flow rate data points whose calculated waveform index is below the predetermined waveform index threshold.

6. The system of claim 5, wherein calculating the non-suction trough baseline from the plurality of flow rate data points includes:
calculating an average non-suction trough baseline from the array of non-suction trough baseline data points; and
subtracting from the calculated average non-suction trough baseline a standard deviation of the calculated average non-suction trough baseline multiplied by a standard deviation factor.

7. The system of claim 6, wherein the standard deviation factor is one.

8. The system of claim 1, wherein the predetermined threshold is equal to one.

9. The system of claim 1, wherein the predetermined waveform index threshold is 0.3 to 0.6.

10. The system of claim 1, wherein the plurality of flow rate data points includes data sampled over 24 hours.

11. The system of claim 1, wherein the plurality of flow rate data points is equal to 96 data points.

12. The system of claim 1, wherein to determine the measure of suction density based on the number of the plurality of flow rate data points for which the suction condition is present and the total number of the plurality of flow rate data points, the processing circuitry is configured to divide the number of the plurality of flow rate data points for which the suction condition is present by the total number of the plurality of flow rate data points.

13. The system of claim 1, wherein the processing circuitry is configured to cause the display device to output an indication of the flow rate.

14. The system of claim 13, wherein the processing circuitry is configured to cause the display device to output the indication of the flow rate concurrently with the indication of the measure of suction density.

15. The system of claim 1, wherein the processing circuitry is further configured to cause the display device to output an indication of a current draw of the motor.

16. The system of claim 1, wherein the controller comprises the display device.

* * * * *